(12) United States Patent
Lewis et al.

(10) Patent No.: US 7,399,968 B2
(45) Date of Patent: Jul. 15, 2008

(54) SPECTROSCOPIC INSTRUMENTS AND METHODS EMPLOYING ARRAY DETECTOR AND VARIABLE FILTERING

(75) Inventors: E. Neil Lewis, Brookville, MD (US); David J. Strachan, Baltimore, MD (US); Linda H. Kidder, Wolney, MD (US)

(73) Assignee: Malvern Instruments Incorporated, Southborough, MA (US)

( * ) Notice: Subject to any disclaimer, the term of this patent is extended or adjusted under 35 U.S.C. 154(b) by 0 days.

(21) Appl. No.: 10/776,029

(22) Filed: Feb. 10, 2004

(65) Prior Publication Data

US 2005/0199788 A1    Sep. 15, 2005

Related U.S. Application Data

(63) Continuation of application No. 09/507,293, filed on Feb. 18, 2000, now Pat. No. 6,690,464.

(60) Provisional application No. 60/120,859, filed on Feb. 19, 1999, provisional application No. 60/143,801, filed on Jul. 14, 1999.

(51) Int. Cl.
   *G01J 3/28* (2006.01)
(52) U.S. Cl. .................. 250/339.12; 250/226; 356/326
(58) Field of Classification Search ................. 250/226, 250/339.12, 339.09; 356/456, 326
See application file for complete search history.

(56) References Cited

U.S. PATENT DOCUMENTS

| | | | |
|---|---|---|---|
| 3,737,239 A | 6/1973 | Adams et al. | 356/177 |
| 3,929,398 A | 12/1975 | Bates | 356/186 |
| 4,004,150 A | 1/1977 | Natelson | 250/328 |
| 4,054,389 A | 10/1977 | Owen | 356/189 |
| 4,278,538 A | 7/1981 | Lawrence et al. | 209/580 |
| 4,599,001 A | 7/1986 | Richard | 356/419 |
| 4,788,428 A | 11/1988 | Metcalf et al. | 250/332 |
| 4,922,092 A | 5/1990 | Rushbrooke et al. | 250/213 |
| 5,007,737 A | 4/1991 | Hirleman, Jr. | 356/336 |

(Continued)

FOREIGN PATENT DOCUMENTS

DE    28 23 514 A    5/1978

(Continued)

OTHER PUBLICATIONS

Akong, M. et al, "High-Throughput Measurement of Intracellular $Ca^{2-}$ by Fluorescence Imaging of a 96-Well Microtiter Plate," *25th Annual Meeting of the Society for Neuroscience, Society for Neuroscience Abstracts*. 21 (1-3). 1995, 577.

(Continued)

*Primary Examiner*—Thanh X. Luu
*Assistant Examiner*—Tony Ko
(74) *Attorney, Agent, or Firm*—Kristofer E. Elbing

(57) ABSTRACT

Disclosed are pharmaceutical dosage unit manufacturing process control apparatus and methods. These can include acquiring a plurality of multi-pixel images of a flow of pharmaceutical dosage units at different wavelengths along an axis that is perpendicular to a direction of the flow of pharmaceutical dosage units, processing the images acquired in the step of acquiring, and providing an indication about the flow of pharmaceutical dosage units based on the step of processing.

28 Claims, 4 Drawing Sheets

U.S. PATENT DOCUMENTS

| | | | |
|---|---|---|---|
| 5,029,245 A | 7/1991 | Keranen et al. | 250/205 |
| 5,166,755 A | 11/1992 | Gat | 356/419 |
| 5,244,630 A | 9/1993 | Khalil et al. | 422/52 |
| 5,257,086 A | 10/1993 | Fateley et al. | 356/328 |
| 5,272,518 A | 12/1993 | Vincent | 356/405 |
| 5,377,003 A | 12/1994 | Lewis et al. | 356/300 |
| 5,379,065 A | 1/1995 | Cutts | 348/269 |
| 5,386,112 A | 1/1995 | Dixon | 250/234 |
| 5,440,388 A * | 8/1995 | Erickson | 356/456 |
| 5,448,069 A | 9/1995 | Tobler et al. | 250/339.01 |
| 5,488,474 A | 1/1996 | Fateley et al. | 356/326 |
| 5,504,332 A | 4/1996 | Richmond et al. | 250/339.12 |
| 5,508,200 A | 4/1996 | Tiffany et al. | 436/44 |
| 5,528,368 A | 6/1996 | Lewis et al. | 356/346 |
| 5,532,128 A | 7/1996 | Eggers et al. | 435/16 |
| 5,545,897 A | 8/1996 | Jack | 250/339.13 |
| 5,558,231 A | 9/1996 | Weier | 209/580 |
| 5,568,266 A | 10/1996 | Ciza et al. | 356/402 |
| 5,579,105 A | 11/1996 | Belton et al. | 356/310 |
| 5,589,351 A | 12/1996 | Harootunian | 435/29 |
| 5,606,413 A | 2/1997 | Bellus et al. | 356/326 |
| 5,615,009 A | 3/1997 | Sakura et al. | 356/326 |
| 5,668,373 A | 9/1997 | Robbat, Jr. et al. | 250/339.12 |
| 5,675,155 A | 10/1997 | Pentoney, Jr. et al. | 250/458.1 |
| 5,790,188 A | 8/1998 | Sun | 348/144 |
| 5,828,066 A | 10/1998 | Messerschmidt | 250/339 |
| 5,880,830 A * | 3/1999 | Schechter | 250/461.1 |
| 5,949,480 A | 9/1999 | Gerhart et al. | 348/135 |
| 6,078,390 A | 6/2000 | Bengtsson | 356/318 |
| 6,118,530 A | 9/2000 | Bouevitch et al. | 356/308 |
| 6,120,518 A | 9/2000 | Mark et al. | 606/170 |
| 6,166,373 A * | 12/2000 | Mao | 250/226 |
| 6,172,743 B1 | 1/2001 | Kley et al. | 356/39 |
| 6,211,906 B1 | 4/2001 | Sun | 348/144 |
| 6,229,913 B1 | 5/2001 | Nayar et al. | 382/154 |
| 6,236,047 B1 | 5/2001 | Malin et al. | 250/339 |
| 6,253,162 B1 | 6/2001 | Jarman et al. | 702/179 |
| 6,313,423 B1 | 11/2001 | Sommer et al. | 209/587 |
| 6,323,944 B1 | 11/2001 | Xiao | 356/73 |
| 6,373,568 B1 | 4/2002 | Miller et al. | 356/326 |
| 6,380,539 B1 | 4/2002 | Edgar | 250/339.05 |
| 6,483,112 B1 | 11/2002 | Lewis | 250/339.05 |
| 6,495,818 B1 | 12/2002 | Mao | 250/226 |
| 2001/0041843 A1 | 11/2001 | Modell et al. | |
| 2004/0021861 A1 * | 2/2004 | Lewis | 356/326 |

FOREIGN PATENT DOCUMENTS

| | | |
|---|---|---|
| EP | 0 887 638 A1 | 12/1998 |
| GB | 2 014 300 A | 8/1979 |
| GB | 2 315 131 A | 1/1998 |
| WO | WO 89 05465 A1 | 6/1989 |
| WO | WO 97 13839 A1 | 9/1996 |
| WO | WO 98 15813 A1 | 4/1998 |
| WO | WO 99 02950 A1 | 1/1999 |
| WO | WO 00 60529 A1 | 10/2000 |

OTHER PUBLICATIONS

Frgala, T; Proffitt. RT: Reynolds, CP. "A novel 96-well plate cyotoxicity assay based on florescence digital imaging microscopy," *Proceedings of the Eighty-sixth Annual Meeting of the American Association for Cancer Research*, 36 (Mar. 1995).

Geladi, Paul and Grahn, Hans. *Multivariate Image Analysis*. John Wiley and Sons, 1997, pp. vii-xiii, 23-44.

Grant, RL; Acosta, D, "Ratiometric measurement of interacellular pH of cultured cells with BCECF in a fluorescence multi-well plate reader," *In Vitro Cell Dev Biol Anim*. 33(4) (Apr. 1997), 256-260.

Hyvarinen, Tymo; Herrala, Esko: and Dall' Ava. Alberto. "Direct sight imaging spectrograph: a unique add-on component brings spectral Imaging to Industrial applications," Presented at 1998 IS&T/SPIE's Symposium on Electronic Imaging: Science and Technology (EI98), in Conference 3302: Digital Solid State Comeras: Design and Applications, Paper 3302-21. Jan. 25-30, 1998, San Jose Convention Center, San Jose, California.

Janssen, EH; Buskens, CA; van den Berg, RH. "Fast Detection of Homogeneous Chemiluminescent Immunoassays with a Sensitive Photoplate," *Journal of Chromatography*, 489 (1989) 245-253.

Mao, Chengye: Seal, Mike; Heitschmidt, Gerald. "Airborne Hyperspectral Image Acquisition with Digital CCD Video Camera," 16th Biennial Workshop on Videography & Color Photography in Resource Assessment (1997), 129-140.

Optical Insights, LLC. "MultiSpec Imager," 1998.

Schullek. John R; Butler, John H; Ni, Zhi-Jie; Chen, Dawn; Yuan, Zhengyu. "A High-Density Screening Format for Encoded Combinatorial Libraries; Assay Miniaturization and Its Application to Enzymatic Reactions," *Analytical Biochemistry*, 246 (1997). 20-29.

Spectral Imaging Ltd. "Specim ImSpector Reference Examples," 1999.

Sun, Xiuhong; Baker, James; Hordon, Richard. "A Spectrally-Filtered Airborne Video SYstem and Its Imagery," 15th Biennial Workshop on Videography & Color Photography in Resource Assessment (1995). 253-257.

* cited by examiner

SPECTROSCOPIC INSTRUMENTS AND METHODS EMPLOYING ARRAY DETECTOR AND VARIABLE FILTERING

CROSS-REFERENCE TO RELATED APPLICATION

This application is a continuation of Application Ser. No. 09/507,293, filed Feb. 18, 2000, now U.S. Pat. No. 6,690,464, which claims the benefit of U.S. Provisional Application Nos. 60/120,859, filed Feb. 19, 1999, and 60/143,801, filed Jul. 14, 1999, which are all herein incorporated by reference.

This application also relates to subject matter described in copending application Ser. No. 09/353,325, filed July 14, 1999, entitled "High-Throughput Infrared Spectrometry," now U.S. Pat. No. 6,483,112 and herein incorporated by reference.

FIELD OF THE INVENTION

This invention pertains to quality control systems and methods that detect process defects in large-scale manufacturing processes, such as the manufacture of pharmaceutical dosage units, using continuous spectral imaging techniques.

BACKGROUND OF THE INVENTION

Defects in pharmaceutical products can be highly dangerous, or even fatal. And even if such defects are relatively minor, such as non-uniformly sized capsules, they can result in a significant loss of goodwill by the manufacturer. It is therefore of the utmost importance to avoid such defects.

Several approaches now exist to screen pharmaceutical agents packaged in predetermined dosage units, such as capsules or tablets. These include off-line and on-line methods. Off-line methods include the testing of samples of reagents and end-products using various analytical methods. On-line methods attempt to monitor the process of manufacturing the product to detect defects as they occur.

A number of on-line screening approaches currently exist. One approach includes adding coloring agents to bulk ingredients and optically checking the shape, integrity, and color of the final product. Systems employing this approach can take a series of video images of dosage units and use image processing methods to assess the shape and color of the dosage units. Other systems employ groups of discrete optical detectors to detect different colors and infrared detectors to detect the scattering caused by structural defects. These systems can be complicated to install and maintain, and cannot guarantee a defect-free product.

SUMMARY OF THE INVENTION

Several aspects of the invention are presented in this application. These relate to improvements to process control apparatus and methods, including apparatus and methods that detect process defects in large-scale manufacturing processes, such as the manufacture of pharmaceutical dosage units, using continuous spectral imaging techniques.

Systems according to the invention are advantageous in that they can continuously test the actual composition of each dosage unit within its packaging. Such systems can therefore screen for errors in coloring of ingredients, for contamination or breakdown that occurs independent of coloring, and for other types of errors that might not otherwise be detected. And because systems according to the invention can perform their composition measurements through the end-user package walls, they can detect contamination or damage that occurs during packaging.

Performing composition analysis by comparing spectral information with libraries of known spectral signatures, allows small concentrations of potentially dangerous contaminants, such as potent toxins, to be detected. Without being correlated to a specific spectral signature, such small concentrations might have little effect on prior art process monitoring methods, and might therefore be dismissed as within an error margin.

Performing composition analysis by comparing spectral information with libraries of known spectral signatures may also allow for the detection of unexpected components. Comparing acquired spectral information with libraries of components may uncover contaminants not normally associated with the process. This may allow a manufacturer to avert hazards that arise out of unforseen circumstances, such as supplier errors or deliberate tampering.

Performing composition analysis by comparing spectral information with libraries of known spectral signatures may further allow for the detection of subtle shifts in the process. Because relative quantities of ingredients can be directly measured, a change in the ratio of these ingredients can be detected. While such changes may not warrant rejection of the products, they may allow the process to be optimized and prevent the process from drifting out of its intending operating range.

Systems according to the invention may also be advantageous in that they can allow a process engineer to select optimal process variables to monitor. By mapping selected spectral information into an image, which is then processed by an image processor, systems according to the invention can apply the image processing resources to the spectral data that correlates best to known and predicted failure modes. And because the system acquires information about a large number of wavelengths simultaneously, a system operator can try a number of different approaches to achieve the best results.

BRIEF DESCRIPTION OF THE DRAWINGS

In the figures, like reference numbers represent like elements.

DESCRIPTION OF AN ILLUSTRATIVE EMBODIMENT

Figure 1:
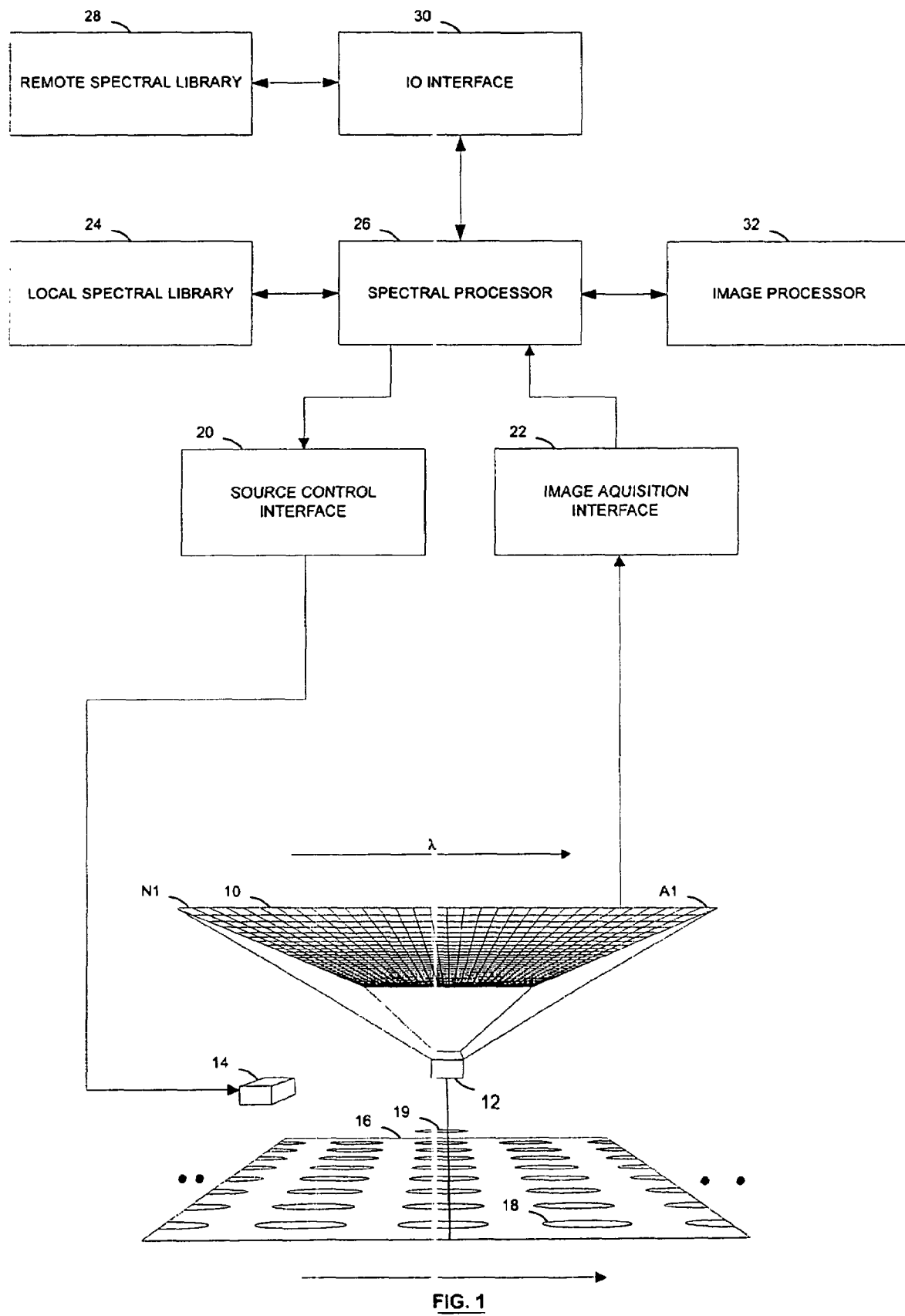
FIG. 1 is a diagram of an embodiment of a pharmaceutical dosage unit manufacturing process control system according to the invention, including a perspective portion illustrating the relationship between the image sensor, the spectrally selective element, and the process stream.

Referring to FIG. 1, a pharmaceutical dosage unit manufacturing process control system according to the invention features an image sensor 10 and a spectrally selective element 12 facing a web 16 that carries a series of parallel rows of pharmaceutical dosage units 18, such as capsules, tablets, pellets, ampoules, or vials, in a process flow direction. For example, the web can carry a continuous stream of blister-packaged tablets from the output of a packaging machine. The image sensor is a multi-element sensor that includes at least a series of adjacent sensing elements located generally along an axis that is perpendicular to the flow direction. The spectrally selective element is a wavelength separating element, and is preferably a dispersive element, such as a diffraction grating or a prism-based monochromator.

Figure 2:
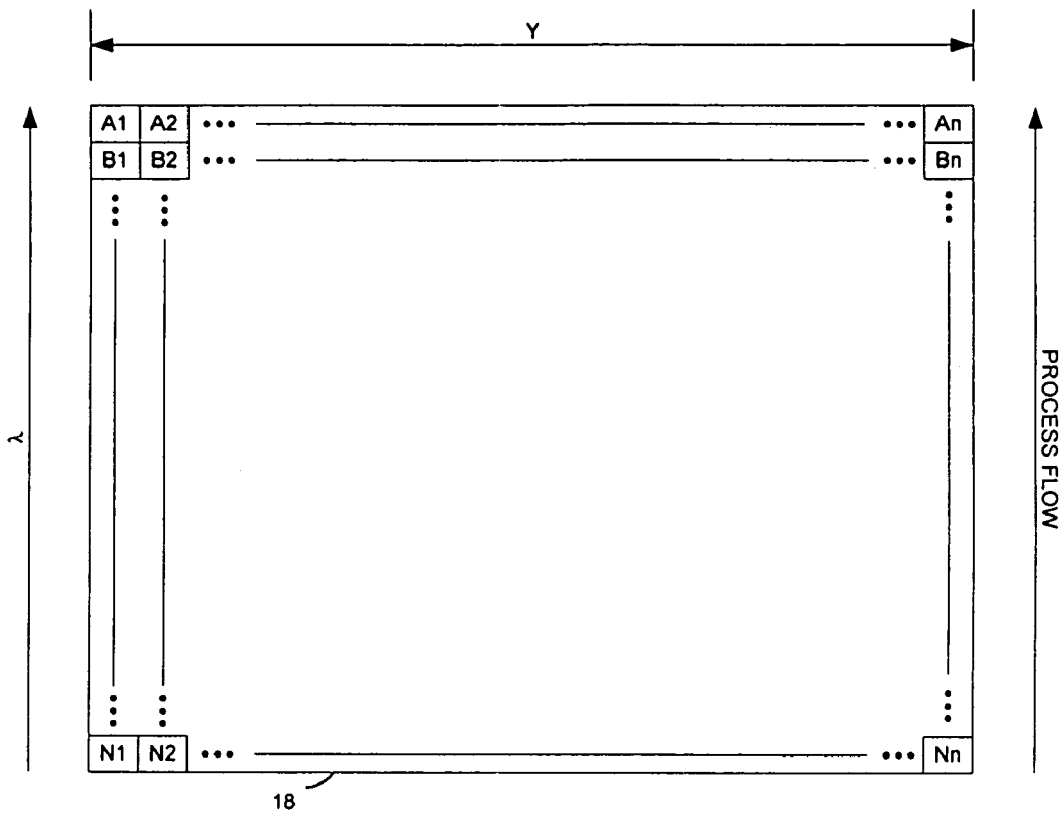
FIG. 2 is a plan view diagram of an image sensor for use with the process control system of FIG. 1.

Referring to FIGS. 1-2, the image sensor 10 is preferably a two-dimensional array sensor that includes a two-dimensional array of detector elements made up of a series of lines of elements (A1-An, B1-Bn, . . . N1-Nn) that are each located generally along an axis that is perpendicular to the flow direction. The image sensor can include an array of integrated semiconductor elements, such as a Charge-Coupled Device (CCD) array, and is preferably sensitive to infrared radiation. Uncooled Idium-Galium-Arsenide (InGaAs) arrays, which are sensitive to near infrared wavelengths, are suitable image sensors, although sensitivity to longer wavelengths would be desirable. It is contemplated that the sensors should preferably have dimensions of at least 64×64 or even 256×256. Where such sensors are not square, they should be oriented with their longer dimension in the direction of the process flow, as spectral information appears to be typically more important than spatial information given the nature of pharmaceutical mass-production equipment.

The system also includes an image acquisition interface 22 having an input port responsive to an output port of the image sensor 10. The image acquisition interface receives and/or formats image signals from the image sensor. It can include an off-the shelf frame buffer card with a 12-16 bit dynamic range, such as are available from Matrox Electronic Systems Ltd. of Montreal, Canada, and Dipix Technologies, of Ottawa, Canada.

A spectral processor 26 has an input responsive to the image acquisition interface 22. This spectral processor has a control output provided to a source control interface 20, which can power and control an illumination source 14. The illumination source for near infrared measurements is preferably a Quartz-Tungsten-Halide lamp.

The spectral processor 26 is also operatively connected to a standard input/output (IO) interface 30 and to a local spectral library 24. The local spectral library includes locally-stored spectral signatures for known process components. These components can include ingredients, process products, or results of process defects or contamination. The IO interface can also operatively connect the spectral processor to a remote spectral library 28.

The spectral processor 26 is operatively connected to an image processor 32 as well. The image processor can be an off-the-shelf programmable industrial image processor, that includes special-purpose image processing hardware and image evaluation routines that are operative to evaluate shapes and colors of manufactured objects in industrial environments. Such systems are available from, for example, Cognex, Inc.

In one embodiment, the system is based on the so-called IBM-PC architecture. The image acquisition interface 22, IO interface 30, and image processor 32 each occupy expansion slots on the system bus. The spectral processor is implemented using special-purpose spectral processing routines loaded on the host processor, and the local spectral library is stored in local mass storage, such as disk storage. Of course, other structures can be used to implement systems according to the invention, including various combinations of dedicated hardware and special-purpose software running on general-purpose hardware. In addition, the various elements and steps described can be reorganized, divided, and combined in different ways without departing from the scope and spirit of the invention. For example, many of the separate operations described above can be performed simultaneously according to well-known pipelining and parallel processing principles.

In operation, referring to FIGS. 1-4, the spectrally selective element 12 is sensitive to the radiation reflected off of a line across the process web 16, and collimated by a first-stage optic, such as a lens (not shown). The spectrally selective element separates the spectral components of the reflected radiation along the axis of the process flow. As a result, the successive lines A1-An, B1-Bn, . . . N1-Nn of the image sensor are exposed to spectral components of the radiation that are of successively higher or lower wavelengths, depending on the relative orientation of the spectrally selective element and the image sensor. In one embodiment, a portion of the line image extends beyond the web to overlap with a stationary reference sample 19 located adjacent the web. This implementation can allow for the removal of transfer of calibration requirements between systems that collect pure component spectra for spectral comparison.

At a predetermined repetition rate, the image acquisition interface 22 acquires a data set representative of the radiation incident on the image sensor (i.e., a spectral line image—step 40). This data set includes image values for each of the pixels along the imaged line on the process web at a number of different wavelengths. In the case of a 256×256 array, intensity values at 256 different wavelengths will be stored for each of 256 points on the imaged line. Once it has been acquired, the image acquisition interface transfers this data set to the spectral processor 26.

The spectral processor 26 then evaluates the acquired spectral line image (step 42). This evaluation can include a variety of univariate and multivariate spectral manipulations. These can include comparing received spectral information with spectral signatures stored in the library, comparing received spectral information attributable to manufactured dosage units with information attributable to the reference sample, or evaluating simplified test functions, such as looking for the absence of a particular wavelength or combination of wavelengths. Multivariate spectral manipulations are discussed in more detail in "Multivariate Image Analysis," by Paul Geladi and Hans, Grahn, available from John Wiley, ISBN No. 0-471-93001-6, which is herein incorporated by reference.

As a result of its evaluation, the spectral processor 26 may detect known components (step 44) and/or unknown components (step 46). If an unknown component is detected, the system records a spectral signature entry for the new component type in the local spectral library 24 (step 48). The system can also attempt to identify the newly detected component in an extended or remote library 28, such as by accessing it through a telephone line or computer network (step 50). The system then flags the detection of the new component to the system operator, and reports any retrieved candidate identities (step 52).

Once component identification is complete, the system maps the different detected components into a color (such as grayscale) line image (step 54). As the system processes further spectral line images, it accumulates a two-dimensional colored image frame. When complete, this image can be transferred to the image processor (step 58), which evaluates the shape and color of the dosage units (step 60), issues rejection signals for rejected dosage units, and compiles operation logs.

Figure 3:
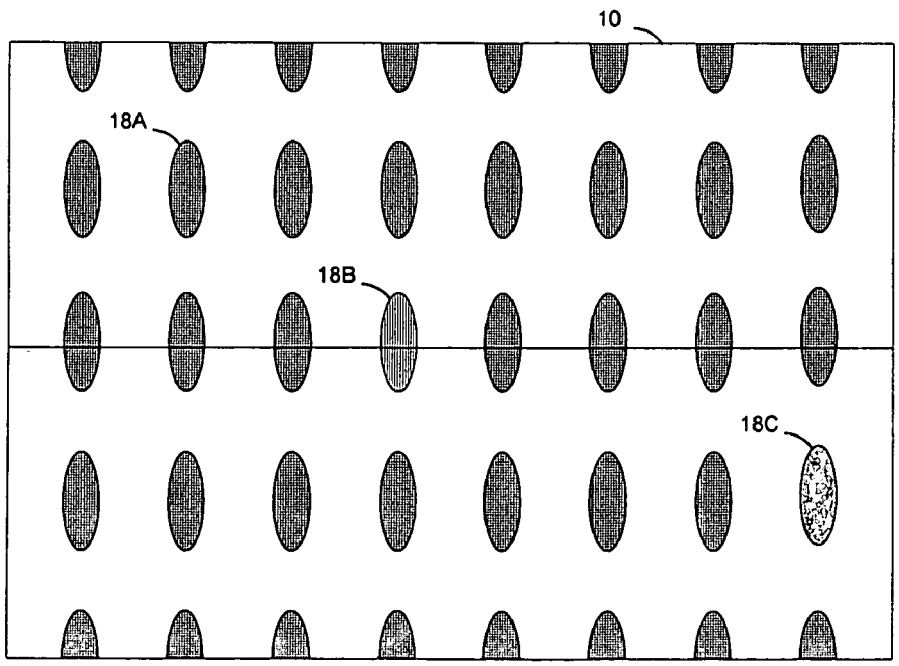
FIG. 3 is a plan view diagram illustrating output of the system of FIG. 1.
Figure 4:
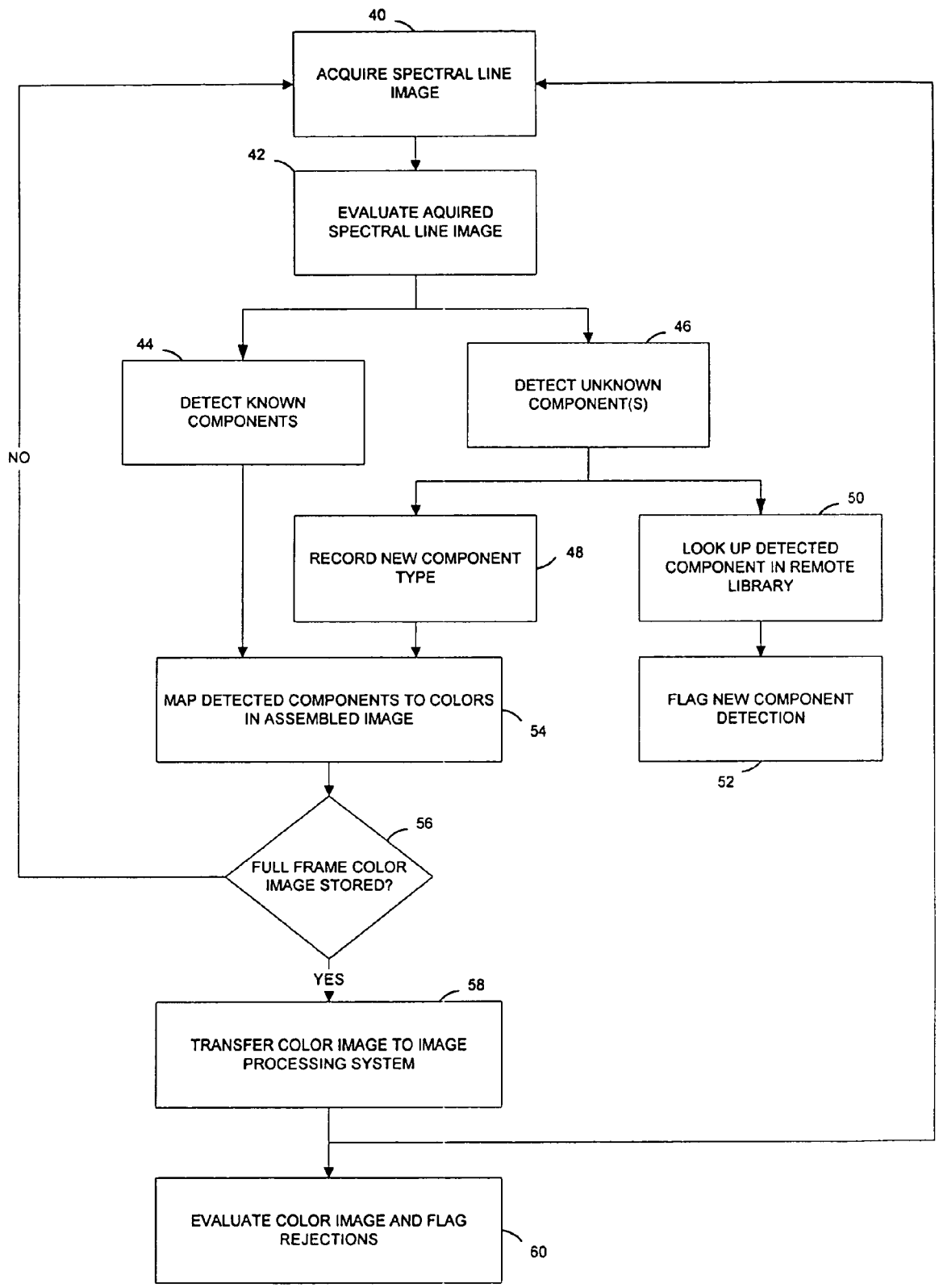
FIG. 4 is a flowchart illustrating the operation of the embodiment of FIG. 1.

As shown in FIG. 3, the color image will resemble the process web, although it may be stretched or squeezed in the direction of the process flow, depending on the acquisition rate. The image can include a color that represents the composition of the web 16. It will can also include colors that represent known good components 18A, colors that represent known defect components 18B, and colors that represent unknown components 18C. The mapping can also take the form of a spectral shift, in which some or all of the acquired spectral components are shifted in a similar manner, preserving the relationship between wavelengths. Note that because the image maps components to colors, it provides information about spatial distribution of the pharmaceutical composition in addition to identifying its components.

While the system can operate in real-time to detect defective products, its results can also be analyzed further off-line. For example, some or all of the spectral data sets, or running averages derived from these data sets can be stored and periodically compared with extensive off-line databases of spectral signatures to detect possible new contaminants. Relative spectral intensities arising from relative amounts of reagents or ingredients can also be computed to determine if the process is optimally adjusted.

Note that the system presented above is self-scanning. Although it can be synchronized with the process by a sensor, such synchronization is not required. The system can therefore be easily retrofit to existing installations and does not require any moving parts.

The acquisition method employed by the process control system can also be computationally efficient. Since data is acquired and spectrally processed on a line-by-line basis, the spectral processor does not have to store large amounts of intermediate results. Once a line has been mapped to a colored line image, all of the acquired data and intermediate results can be discarded, and a new line processed. This can allow the system to operate in real time with relatively simple computer components, keeping the overall system cost low.

Figure 5:
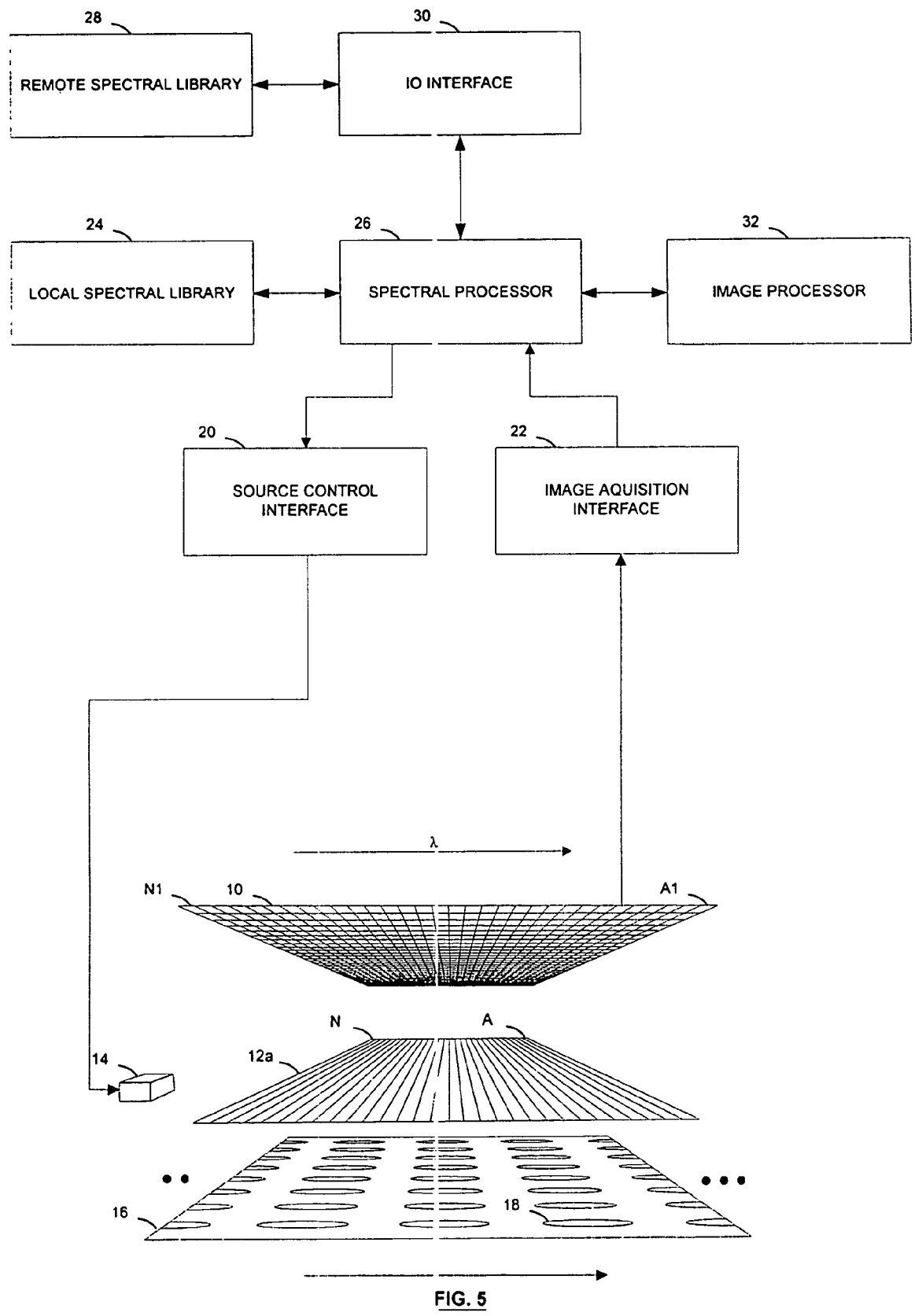
FIG. 5 is a diagram of a second embodiment of a pharmaceutical dosage unit manufacturing process control system according to the invention, including a perspective portion illustrating the relationship between the image sensor, the spectrally selective element, and the process stream.

Referring to FIG. 5, a second embodiment of a pharmaceutical dosage unit manufacturing process control system according to the invention includes a variable-bandpass filter 12a between the two-dimensional array sensor and the process stream. This filter has a narrow pass-band with a center wavelength that varies along the process direction. The leading edge A of the filter passes shorter wavelengths, and as the distance from the leading edge along the process flow direction increases, the filter passes successively longer wavelengths. At the trailing edge N of the filter, the filter passes a narrow range of the longest wavelengths. The orientation of the filter can also be reversed, so that the pass-band center wavelength decreases along the process flow direction. Although the filter has been illustrated as a series of strips located perpendicular to the process flow direction, it can be manufactured in practice by continuously varying the dielectric thickness in an interference filter. Preferably, the filter should have a range of pass-bands that matches the range of the camera. Suitable filters are available, for example, from Optical Coatings Laboratory, Inc. of Santa Rosa, Calif.

In operation of this embodiment, acquisition interface 22 acquires data representing a series of variably-filtered, two-dimensional images. These two-dimensional images each include image values for the pixels in a series of adjacent lines perpendicular to the process web. Because of the action of the variable-bandpass filter, the detected line images that make up each two-dimensional image will have a spectral content that varies along the process direction.

The variably filtered images are combined as they are acquired in order to obtain full-range spectral images. As each imaged line progresses along the web, each successive line (N1 ... A1) of elements in the array sensor 10 will sense radiation that has been filtered through a corresponding line (N ... A) of the filter. These individual line images can be assembled to create a full-spectrum line image. The assembly can take place by itself, or in combination with other operations, such as digital filtering operations. This embodiment is particularly advantageous because the variable-bandpass filter is relatively inexpensive and robust.

Another approach involves the use of an optical system that simultaneously projects a number of spectrally-discrete versions of the same two-dimensional image onto the array sensor 10. Such systems are described in PCT application No. PCT/US98/14218 published under No. WO09902950, which are herein incorporated by reference. The use of these systems is advantageous in that they allow high data throughputs for a given web speed, without adding moving parts. Systems of this type are available from Optical Insights, Inc of Tucson, Ariz.

A further embodiment employs multi-source arrays to provide successive illumination at different wavelengths and thereby obtain spectral information from the process. Such arrays are described in a copending provisional application entitled "Multi-Source Arrays," filed on the same day as this application, and herein incorporated by reference.

The present invention has now been described in connection with a number of specific embodiments thereof. However, numerous modifications which are contemplated as falling within the scope of the present invention should now be apparent to those skilled in the art. For example, aspects of the invention may also be applicable to other types of manufacturing processes, such in detecting the presence of undesirable by-products in the manufacture of plastic articles. In addition, while a two-dimensional image sensor with a dispersive or graded spectrally selective element is at present contemplated to be the best approach to acquiring line image data, a one-dimensional image sensor coupled with a high-speed filtering system might allow a suitable amount of data to be acquired in some circumstances. Therefore, it is intended that the scope of the present invention be limited only by the scope of the claims appended hereto. In addition, the order of presentation of the claims should not be construed to limit the scope of any particular term in the claims.

What is claimed is:

1. A two-dimensional imaging optical instrument for acquiring images of a two-dimensional sample area, comprising:
    a two-dimensional spatial detector having detector elements aligned along a first axis and a second axis,
    a two-dimensional variable filter having filter characteristics that vary in at least one dimension, and being located in an optical path between the two-dimensional sample area and the two-dimensional spatial detector,
    wherein the instrument defines the optical path as a two-dimensional optical path that simultaneously conveys radiation from different positions in the sample area to different detector elements through portions of the spatial detector having different ones of the filter characteristics to produce variably filtered images, and
    a spectral processor operative to combine spectral information from a plurality of the variably filtered two-dimensional images obtained from the two-dimensional spatial detector as the two-dimensional sample area moves with respect to the instrument.

2. The apparatus of claim 1 wherein the variable filter is a variable band-pass filter.

3. The apparatus of claim 1 wherein the variable filter is a continuously variable filter.

4. The apparatus of claim 1 further including an infrared source and wherein the spatial detector is an infrared detector.

5. The apparatus of claim 1 further including a near infrared source and wherein the spatial detector is a near infrared detector.

6. The apparatus of claim 1 further including an ultraviolet source and wherein the spatial detector is an ultraviolet detector.

7. The apparatus of claim 1 further including a visible light source and wherein the spatial detector is a visible light detector.

8. The apparatus of claim 1 further including means for moving the sample area relative to the spatial detector.

9. The apparatus of claim 1 further including logic responsive to the spatial detector for combining a series of images from the spatial detector to obtain full-range spectral images.

10. The apparatus of claim 1 further including a first stage optic between the sample area and the detector.

11. The apparatus of claim 1 further including logic responsive to the detector to selectively display spectral information tat relates to at least one predetermined substance in the sample area.

12. The apparatus of claim 1 further including multivariate spectral analysis logic responsive to the detector.

13. The apparatus of claim 1 wherein the spatial detector is an integrated semiconductor array detector.

14. The apparatus of claim 1 wherein the instrument is located proximate a moving sample flow.

15. The apparatus of claim 1 further including an image acquisition interface that acquires images at a rate that is independent of a rate of movement of the sample area.

16. The apparatus of claim 1 wherein the processor combines the images in real time as they are acquired.

17. The apparatus of claim 1 wherein the instrument is operable independent of any moving parts.

18. An optical method, comprising:
   substantially simultaneously filtering a plurality of radiation beam portions from a first set of different positions in a sample area with different filter characteristics,
   substantially simultaneously detecting the plurality of radiation beam portions with different parts of a spatial detector after filtering the radiation beam portions in the step of filtering to detect a first variably filtered image,
   moving the sample area,
   after the step of moving, again substantially simultaneously filtering a plurality of radiation beam portions from a second set of positions in the sample area with different filter characteristics, wherein the first set of positions is different from the second set of positions,
   again substantially simultaneously detecting the plurality of radiation beam portions with different parts of the spatial detector after filtering the radiation beam portions in the step of again filtering to detect a second variably filtered image, and
   combining results of the steps of simultaneously detecting and again simultaneously detecting.

19. The method of claim 18 wherein the steps of detecting acquire data representing a series of variably filtered two-dimensional images, and further including a step of combining portions of the variably filtered images to obtain spectral images.

20. The method of claim 19 wherein the steps of filtering and detecting are applied to radiation from a pharmaceutical composition and wherein the step of combining derives a spectral image descriptive of the contents of the pharmaceutical composition.

21. The method of claim 19 wherein the step of combining results in one or more infrared images.

22. The method of claim 19 wherein the step of combining results in one or more near-infrared images.

23. The method of claim 18 further including a step of performing a multivariate spectral analysis on results of the steps of detecting.

24. The method of claim 18 further including a step of selectively displaying spectral information that relates to at least one predetermined substance in the sample area.

25. The method of claim 18 further including a step of providing a reference substance in the sample area.

26. The method of claim 18 wherein the steps of detecting take place at a rate that is independent of a rate of movement of the sample area.

27. The method of claim 18 wherein the step of combining operates in real time as the beam portions are detected.

28. The method of claim 18 wherein the method is operable independent of any moving parts.

* * * * *